United States Patent [19]

Tsao

[11] Patent Number: 5,019,044

[45] Date of Patent: May 28, 1991

[54] SAFETY HYPODERMIC SYRINGE

[76] Inventor: Chien-Hua Tsao, No. 326, Pa Te Road, Sec. 2, Taipei, Taiwan

[21] Appl. No.: 393,390

[22] Filed: Aug. 14, 1989

[51] Int. Cl.$^5$ ............................................. A61M 5/00
[52] U.S. Cl. .................................... 604/110; 604/195
[58] Field of Search ............... 604/110, 187, 136, 218, 604/220, 195

[56] References Cited

U.S. PATENT DOCUMENTS

| | | | |
|---|---|---|---|
| 4,781,684 | 11/1988 | Trenner | 604/110 |
| 4,838,869 | 6/1989 | Allard | 604/110 |

Primary Examiner—John D. Yasko
Attorney, Agent, or Firm—Asian Pacific Int'l Patent & Trademark Office

[57] ABSTRACT

A safety hypodermic syringe includes a hypodermic needle fixedly connected to holder plate and constantly supported by a spring means for making axial movement, which holder plate is normally retained by a clamping means at a ready position for injection. When a plunger is pushed to the front limit, the hypodermic needle becomes released from the constraint of the clamping means and pushed by the spring means to drop and to further follow a rubber plug to be squeezed into the inner chamber of the plunger so as to isolate from outside and to prevent from pricking accident or possible body fluid contact.

4 Claims, 4 Drawing Sheets

SAFETY HYPODERMIC SYRINGE

BACKGROUND OF THE INVENTION

The present invention is related to a kind of hypodermic syringe and more particularly to a safety hypodermic syringe in which the hypodermic needle will be automatically concealed therein after injection process is performed.

The hypodermic syringes currently in use are normally disposable and made of plastic material, which are proposed for single shot application and shall be thrown away immediately after use so as to prevent from body fluid contact.

This kind of conventional plastic syringe will have little change in structure before and after injection. Therefore, mistake tends to happen and a disposed syringe may be repeatedly used, for in order to save the cost, some evil-doers may wash the used syringes for further use. As everybody knows, it is quite dangerous to repeatedly use a hypodermic syringe since infections such as AIDS and hepatitis may be infected through body fluid contact.

Another disadvantage of the conventional disposable hypodermic syringe is the high frequency of pricking accident to the nurse during operation. According to the prior art, the hypodermic needle is normally protected by a needle cap, which shall be removed from the hypodermic needle when to suck up liquid medicine. After injection the needle cap shall be mounted on the hypodermic needle before the syringe is thrown away, so as to prevent from pricking accident to the person who handle the refuse. However, because the boring bore of a needle cap is very small the hypodermic is difficult to insert. Therefore, pricking accident may be happened during the operation to remount a needle cap onto a hypodermic needle, which pricking accident will more frequently happen when a nurse is under emergency condition or high working pressure. According to the report from Morbidity and Mortality Weekly Report (Vol. 36, No. 2S) issued on Aug. 21, 1987 by the Department of Health of the U.S. Government, there was disclosed 708 persons having ever been injured by hypodermic needle among the total 883 investigated, i.e., 80% of the investigated having every been pricked by hypodermic needle. Further, according to the report from The New England Journal of Medicine (Vol. 31), it is a high risk matter to be injured by hypodermic needle since infections such as AIDS and hepatitis may be infected through body fluid contact.

Further, according to the statistics on AIDS cases issued by the Department of Health of the U.S. Government, up to May 1988 there were 68,052 AIDS patients reported, among which 34,088 were died. It is estimated that there will be as much as one and half million AIDS carrier patients in 1991. Therefore, it is very important to protect medical treatment and nursing people and medical refuse handling people against body fluid contact.

SUMMARY OF THE INVENTION

The main object of the present invention is to provide a safety hypodermic syringe in which the hypodermic needle will be automatically dropping into the inner chamber of the plunger to isolate from contact of people for easy handling to throw away, so as to prevent from body fluid contact.

Another object of the present invention is to provide a safety hypodermic syringe which will be changed in outer appearance and the hypodermic needle will be completely concealed from outside when it is used, so as to help nursing people as well as patient simply identify if a syringe is a new one or has been used.

Therefore, a safety hypodermic syringe which achieves the said and other objects is including a barrel for containing liquid medicine; a hollow plunger blocked up with a rubber plug, said hollow plunger having integrally connected thereto a ring-shaped plunger element being set in the barrel to slide along axial way; and a clamping means having a spring means mounted thereon to constantly support the hypodermic needle in a ready position for injection. When in operation, the plunger is pushed ahead to inject the liquid medicine into patient's body through the hypodermic needle. As soon as the plunger is pushed to the front limit, the clamping means is squeezed by the plunger to break away from its clamping position and to let the hypodermic needle be released from the clamping force and to be immediately forced into the inner chamber of the plunger by the spring means. Therefore, the hypodermic needle becomes completely concealed from outside to prevent from body fluid contact.

BRIEF DESCRIPTION OF THE DRAWINGS

The drawings disclose an illustrative embodiment of the present invention which serves to exemplify the various advantages and objects hereof, and are as follows.

DETAILED DESCRIPTION OF THE PREFERRED EMBODIMENT

Figure 1:
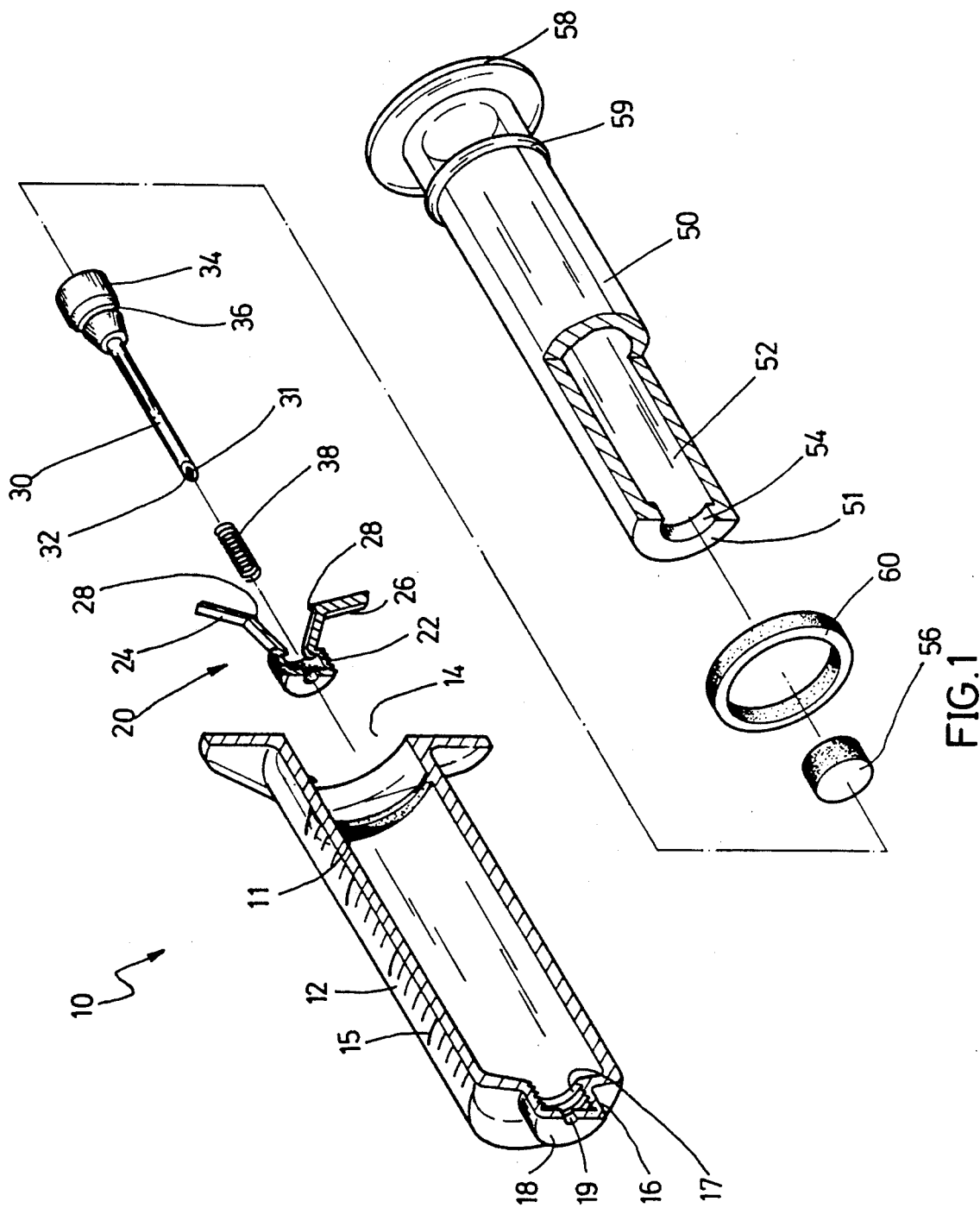
FIG. 1 is a perspective exploded and partly sectional view of a safety hypodermic syringe embodying the present invention.
Figure 2:
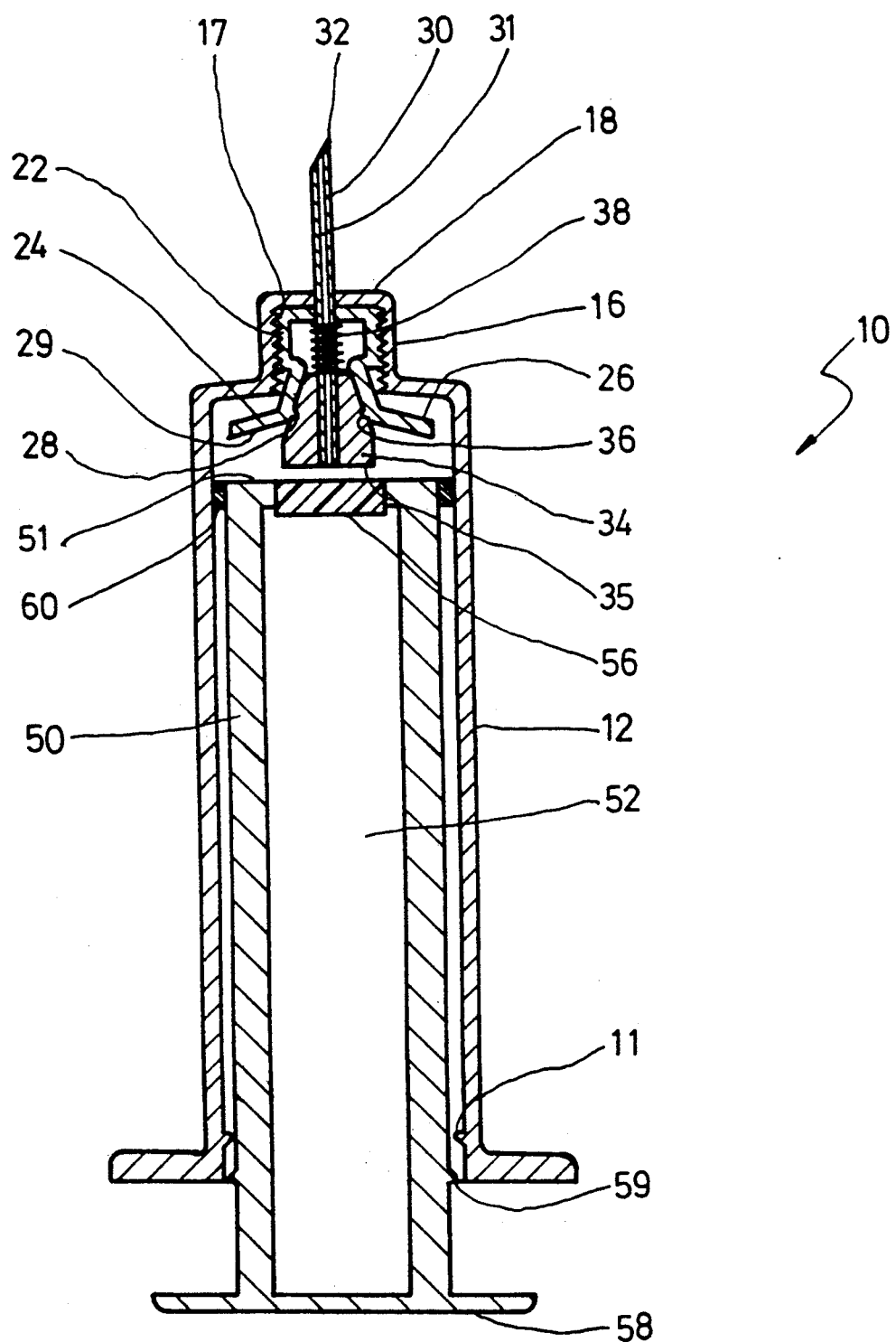
FIG. 2 is a sectional assembly view of the said safety hypodermic syringe before injection.

Referring to FIGS. 1 and 2, a safety hypodermic syringe 10 is including a barrel 12 for containing liquid medicine, which barrel 12 comprises an opening 14 at the rear end and a neck portion 16 in reduced diameter at the front end, which neck portion 16 is having an inner thread 17 and comprising an axial hole 19 through which a hypodermic needle is passing. An elastic clamping means 20 is connected to the barrel 12 at the inner side by means of screw-joint, having integrally a cylindrical front half portion comprising an outer thread 22 for connection with the inner thread 17 by means of screw joint, and a rear half portion comprised of two L-shaped clamping elements 24 and 26, which elastic clamping means 20 provides elastic resilience to clamping inward. A hypodermic needle 30 which is fixedly connected to a holder plate 34 firmly retained by the two elastic clamping elements 24 and 26 is having internally a passage through which liquid medicine is passing, and a pointed front end 32, which serves as a means to insert into patient's muscle for injection of liquid medicine from the barrel 12 through the passage 31 into patient's body. In order to reinforce the clamping effect of the clamping elements 24 and 26 on the holder plate 34, the clamping elements 24 and 26 are having flanges 28 made thereon to respectively engage with the recesses 36 which are made on the holder plate 34. Therefore, under normal condition when the two clamping elements are not pried to open by outside force, the holder plate 34 will be firmly retained by the elastic clamping means 20 by means of the engagement of the flanges 28 with the recesses 36 and the property of constantly inward clamping force of the clamping means 20 itself, so as to let the hypodermic needle 30 protrude beyond the axial hole 19 of the barrel 12 to become in a ready position for injection. A spring means 38 is mounted on the hypodermic needle 30 and set between the holder plate 34 and the outer threaded cylindrical front half portion 22, which spring means 38 gives a spring force to the holder plate 34 to slide along axial way. Under normal condition, the spring force that the spring means 38 provides is conquered by the clamping force that the two clamping means 24 and 26 provide. Therefore, the spring force will not be in effect before injection process is performed. The safety syringe 10 is further comprising a plunger 50 having a ring-shaped plunger element 60 integrally made at the front by means of heat-sealing or any other suitable processing process. The plunger assembly which is formed of the plunger 50 and the ring-shaped plunger element 60 may be set into the barrel 12 from the opening 14 by means of push force to slide therein along axial way, to let the front end surface 51 of the plunger 50 and the ring-shaped plunger element 60 collectively block up the opening 14 of the barrel 12. Therefore, through the axial movement of the plunger 50 and the ring-shaped plunger element 60, liquid medicine may be sucked up into the barrel 12 or the liquid medicine in the barrel 12 may be injected through the passage 31 of the hypodermic needle 30. According to the present invention, the plunger 50 is having an inner chamber 52, a front opening 54 on the front end surface 51 to communicate with the inner chamber 52, which front opening 54 is normally sealed by a rubber plug 56, and an enclosed handle portion 58 for holding of hand.

The hypodermic needle 30 which is protruding beyond the barrel 12 may be enclosed by a needle cap (not shown) to protect against pricking accident and prevent from contamination.

Please refer to FIG. 2 again. When injection process is not performed yet, the needle connected holder plate 34 is firmly retained by the clamping means 20 to a ready position. When in use, the plunger 50 is pulled backward to produce a vacuum suction so as to suck up prepared liquid medicine into the barrel 12 through the passage 31.

When to start injection, the pointed front end 32 of the hypodermic needle 30 is piercing into patient's body. When the hypodermic needle 30 pierces through patient's skin, the reactive force on the hypodermic needle 30 will be absorbed by the clamping force that the clamping means 20 applies on the holder plate 34. As soon as the plunger 50 is pushed ahead, the liquid medicine in the barrel 12 is forced to inject through the passage 31 into patient's body.

Figure 3:
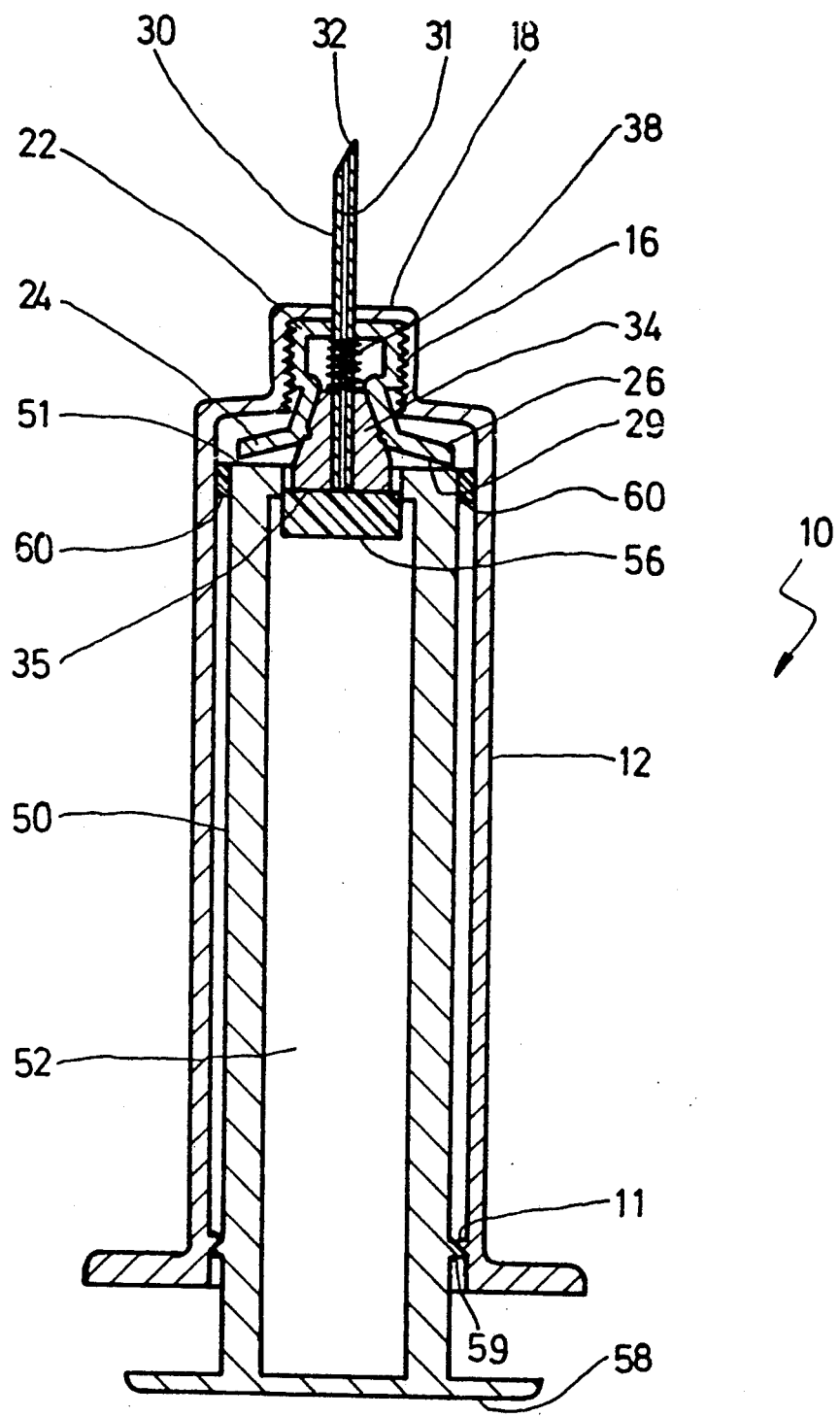
FIG. 3 is a sectional assembly view of the said safety hypodermic syringe when it is at a condition about to finish an injection.

With reference to FIG. 3, when the plunger 50 is pushed toward the front limit, before the bottom surface 29 of the two clamping elements 24 and 26 are in contact with the plunger 50, the bottom surface 35 of the holder plate 34 will be firstly in contact with the rubber plug 58 which blocks up the front opening 54 of the plunger 50. Therefore, as soon as the plunger 50 is pushed to the front limit, the rubber plug 58 is pushed to break away from the front opening 54.

Figure 4:
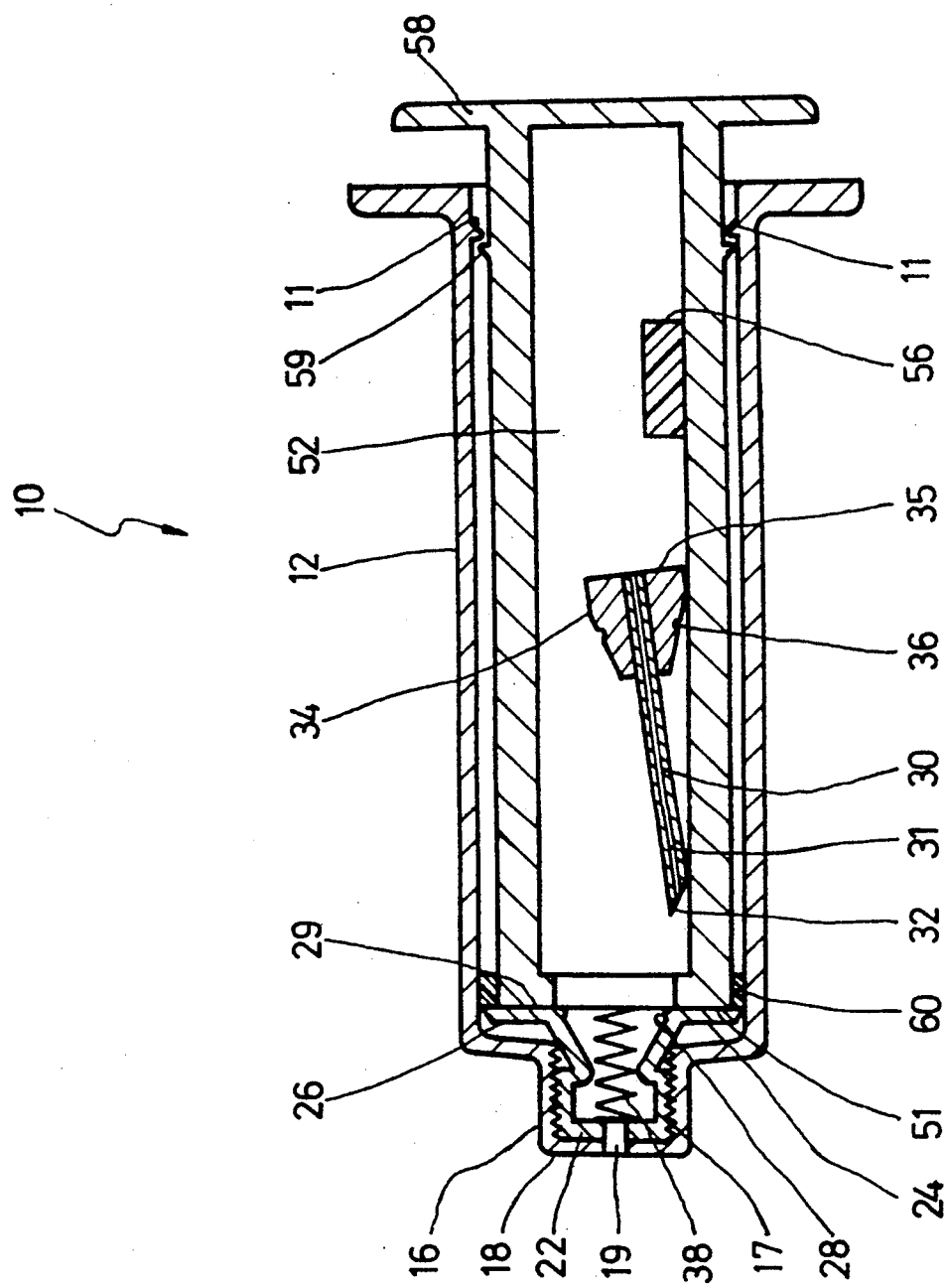
FIG. 4 is a sectional view of the said safety hypodermic syringe after injection therein the hypodermic needle drops into the hollow plunger assembly.

With reference to FIG. 4, when the plunger 50 is pushed to the front limit, the rubber plug 56 is squeezed out of the front opening 54, and the front end surface 51 of the plunger 50 is pressing bottom surface 29 of the two L-shaped clamping elements 24 and 26 to pry them to open and to let the flanges 28 break away from the respective engaged position with the recesses 36, so as to let the holder plate 34 be released from the constraint of the clamping means 20. Under this condition, only the muscle of the patient (not shown) provides a retaining force to hold the hypodermic needle 30 to let the hypodermic needle 30 and the connected holder plate 34 be temporarily retained in an injection position. After injection process is completed, the hypodermic needle 30 of the syringe 10 is pulled out of patient's body, the spring force from the spring 38 will immediately push the holder plate 34 to carry the hypodermic needle 30 to move backward along axial way. Because the rubber plug 56 has been squeezed out of the front opening 54, the hypodermic needle 30 will be pushed by the spring 38 into the inner chamber 52 of the plunger 50 to become totally received therein.

According to the present invention, the barrel 12 and the plunger 50 are having wedge rings 11 and 59 matching with each other to stop against return stroke of the plunger 50 when the plunger 50 is pushed to the front limit, so as to prevent from breaking away of the plunger 50 from the barrel 12 and to reduce space consumption of the used syringe.

The barrel 12 is having volume scale 15 made on the outer wall surface for identification of the amount of liquid medicine filled in the barrel.

As disclosed in the annexed drawings from FIG. 2 through 4, when a nurse pulls the hypodermic needle 30 and the syringe 10 out of patient's body to complete injection process, the holder plate 34 of the hypodermic needle 30 becomes in a freely disposed position without having any clamping force applied thereto and is immediately pushed by the spring means 36 into the inner chamber 52 of the plunger 50 to conceal therein. Therefore, after having completed an injection, the used syringe is well protected to isolate the hypodermic needle from contact of people so as to prevent from pricking accident or body fluid contact.

Having described my invention as related to the embodiment shown in the accompanying drawings, it is my intention that the invention be not limited by any of the details of description, unless otherwise specified, but rather be construed broadly within its spirit and scope as set out in the appended claims.

What is claimed is:

1. A safety hypodermic syringe, including:
   a barrel for containing liquid medicine, having a rear opening and a front neck portion in reduced diameter;
   a clamping means fixed set in said neck portion comprising resilient clamping portion constantly clamping inward;
   a holder plate integrally incorporated with a hypodermic needle, said holder plate being firmly retained by said clamping portion of said clamping means to let said hypodermic needle protrude beyond said barrel to become in a ready position for injection;
   a spring means being to give a spring force to said hypodermic needle connected holder plate so as to let said hypodermic needle connected holder plate slide along axial way; and a hollow plunger having at lest a part inserted through said rear opening and received in said barrel to slide therein by means of pressure force, said plunger comprising a front end surface having thereon an axial hole communicating with its inner chamber, said axial hole being blocked up by a rubber plug;

characterized in that when said plunger is pushed toward the front end of said barrel, said rubber plug is squeezed out of said axial hole by said holder plate, and said plunger having its front end press on said clamping means to let said clamping portion be squeezed to open so as to let said holder plate be released from the constraint of said clamping means.

2. The safety hypodermic syringe as set forth in claim 1, wherein said plunger is having a check member to stop against return stroke when said plunger is pushed to the front limit in said barrel.

3. The safety hypodermic syringe as set forth in claim 2, wherein said check member is comprised of two wedge rings respectively made on the inner wall surface of said barrel and the outer wall surface of said plunger to engage with each other.

4. The safety hypodermic syringe as set forth in claim 1, wherein said clamping means is having retainer flanges made thereon at the contact area with said holder plate, and said holder plate is having recesses made thereon to respectively engage with said retainer flanges when said holder plate is retained by said clamping means.

* * * * *